(12) United States Patent
Schroeder

(10) Patent No.: US 10,507,360 B2
(45) Date of Patent: Dec. 17, 2019

(54) POSTURE CORRECTION AND WEIGHT BALANCE APPARATUS

(71) Applicant: William Schroeder, Hollidaysburg, PA (US)

(72) Inventor: William Schroeder, Hollidaysburg, PA (US)

(*) Notice: Subject to any disclaimer, the term of this patent is extended or adjusted under 35 U.S.C. 154(b) by 0 days.

(21) Appl. No.: 16/282,030

(22) Filed: Feb. 21, 2019

(65) Prior Publication Data

US 2019/0255388 A1  Aug. 22, 2019

Related U.S. Application Data

(60) Provisional application No. 62/633,229, filed on Feb. 21, 2018.

(51) Int. Cl.
| | |
|---|---|
| *A63B 26/00* | (2006.01) |
| *A63B 24/00* | (2006.01) |
| *A61B 5/00* | (2006.01) |
| *A61B 5/11* | (2006.01) |
| *G01G 19/44* | (2006.01) |
| *A63B 71/06* | (2006.01) |
| *A61B 5/103* | (2006.01) |
| *A61H 1/00* | (2006.01) |

(52) U.S. Cl.
CPC .......... *A63B 26/003* (2013.01); *A61B 5/0079* (2013.01); *A63B 24/0087* (2013.01); *A61B 5/1036* (2013.01); *A61B 5/1116* (2013.01); *A61B 5/1128* (2013.01); *A61B 5/4561* (2013.01); *A61B 5/4836* (2013.01); *A61B 2505/09* (2013.01); *A61H 1/00* (2013.01); *A61H 2201/164* (2013.01); *A61H 2201/5061* (2013.01); *A63B 2071/0647* (2013.01); *G01G 19/44* (2013.01)

(58) Field of Classification Search
CPC ... A61B 5/4561; A61B 5/1128; A61B 5/1116; A63B 26/003; A63B 24/0087; G01G 19/44; A61H 2201/164
See application file for complete search history.

(56) References Cited

U.S. PATENT DOCUMENTS

| | | | | |
|---|---|---|---|---|
| 3,627,069 A | * | 12/1971 | Ray .................. | G01G 23/32 |
| | | | | 177/210 FP |
| 4,927,138 A | * | 5/1990 | Ferrari .............. | A63B 69/0035 |
| | | | | 482/41 |
| 4,986,534 A | * | 1/1991 | Meier ................ | A61B 5/1036 |
| | | | | 482/8 |

(Continued)

*Primary Examiner* — Sean P Dougherty

(57) ABSTRACT

A posture correction and weight balance apparatus includes a back support, a scale body, and a reflective body. The scale body includes a base, a left platform, a right platform, at least one first display, a left weight sensor, and a right weight sensor. The back support and the reflective body are oppositely positioned of each other about the scale body and terminally and perpendicularly attached to the base. The left platform and the right platform are adjacently aligned across the back support and mounted onto the base. The at least one first display is positioned adjacent to the reflective body and mounted onto the base. The left platform is electronically connected to the at least one first display through the left weight sensor. The right platform is electronically connected to the at least one first display through the right weight sensor.

15 Claims, 12 Drawing Sheets

(56) References Cited

U.S. PATENT DOCUMENTS

| | | | | |
|---|---|---|---|---|
| 5,020,236 | A * | 6/1991 | Kauer | G01B 7/14 |
| | | | | 33/700 |
| 8,301,221 | B2 * | 10/2012 | DiSilvestro | A61B 5/055 |
| | | | | 600/407 |
| 8,723,944 | B1 * | 5/2014 | Imbrock | G01B 17/025 |
| | | | | 324/663 |
| 9,066,021 | B2 * | 6/2015 | Jorgensen | G02B 27/024 |
| 9,173,508 | B2 * | 11/2015 | Tornwall | A47F 9/047 |
| 9,987,188 | B1 * | 6/2018 | Diao | A61H 3/008 |
| 10,258,259 | B1 * | 4/2019 | Zets | A61B 5/1124 |
| 10,300,337 | B2 * | 5/2019 | Nakashima | A61H 1/0244 |
| 2001/0027995 | A1 * | 10/2001 | Patel | G06K 7/10861 |
| | | | | 235/383 |
| 2004/0118191 | A1 * | 6/2004 | Elrod | G01Q 60/32 |
| | | | | 73/105 |
| 2004/0236547 | A1 * | 11/2004 | Rappaport | G06F 17/509 |
| | | | | 703/2 |
| 2008/0147511 | A1 * | 6/2008 | Edwards | G06Q 20/206 |
| | | | | 705/18 |
| 2010/0246898 | A1 * | 9/2010 | Izumi | A63B 6/00 |
| | | | | 382/106 |
| 2013/0171601 | A1 * | 7/2013 | Yuasa | A61B 5/1114 |
| | | | | 434/258 |
| 2014/0347491 | A1 * | 11/2014 | Connor | A61B 5/1114 |
| | | | | 348/158 |
| 2014/0349256 | A1 * | 11/2014 | Connor | G09B 19/0092 |
| | | | | 434/127 |
| 2014/0349257 | A1 * | 11/2014 | Connor | G09B 19/0092 |
| | | | | 434/127 |
| 2015/0126873 | A1 * | 5/2015 | Connor | A61B 5/4866 |
| | | | | 600/475 |
| 2015/0168365 | A1 * | 6/2015 | Connor | G01N 33/02 |
| | | | | 356/51 |
| 2015/0279113 | A1 * | 10/2015 | Knorr | G06T 19/006 |
| | | | | 345/633 |
| 2016/0073886 | A1 * | 3/2016 | Connor | G09B 19/0092 |
| | | | | 600/475 |
| 2016/0140870 | A1 * | 5/2016 | Connor | G09B 19/0092 |
| | | | | 356/51 |
| 2017/0027803 | A1 * | 2/2017 | Agrawal | A61B 5/6828 |
| 2017/0065849 | A1 * | 3/2017 | Konishi | A61B 5/6828 |
| 2017/0206691 | A1 * | 7/2017 | Harrises | G06T 11/60 |
| 2018/0080766 | A1 * | 3/2018 | Johnson | G01S 17/02 |
| 2018/0209178 | A1 * | 7/2018 | Warnbring | E05B 73/0017 |
| 2019/0150792 | A1 * | 5/2019 | Nakashima | A63B 21/00178 |

* cited by examiner

POSTURE CORRECTION AND WEIGHT BALANCE APPARATUS

The current application claims a priority to the U.S. Provisional Patent application Ser. No. 62/633,229 filed on Feb. 21, 2018.

FIELD OF THE INVENTION

The present invention relates generally to a posture correction and weight balance apparatus. More specifically, the present invention allows patients to straighten up their posture while re-educating the body of how to stand correctly with the proper balance, coordination, and weight distribution.

BACKGROUND OF THE INVENTION

Over the years, the health benefits and importance of correct body posture have been forgotten or ignored. With more people spending more time sitting down or walking while looking down at their phones, body posture for many people has been worsened over time. Many people do not realize the health problems bad body posture can cause. Some of the health problems bad posture can cause are back pain, body aches and pain, muscle fatigue, headaches, etc. Recently, people have tried to correct their posture by changing their habits such as sitting with their backs straight, obtaining standing desks for their offices, and other changes which force people to have the correct posture while performing different activities. Another way people have tried to improve their posture is through the use of posture corrective devices. Most of these devices are wearable devices which the user wears around the upper torso to force the user to keep a straight back while performing various activities. While effective at improving the posture, these devices are not often comfortable to wear and can be inconvenient at times, so a device which can be used at home would be more convenient. Furthermore, most of these devices do not provide a feedback system or learning mechanism which allows the user to keep track of their posture and train or educate the body on how to stand correctly with the proper balance. Thus, a device which can be used at home to allow users to straighten up their posture while re-educating the body of how to stand correctly with the proper balance, coordination, and weight distribution is beneficial and necessary.

An objective of the present invention is to straighten up user's posture. Another objective of the present invention is to re-educate the user's body how to stand correctly with the proper balance, coordination, and weight distribution to be equally placed bilaterally. Another objective of the present invention is to be used at home and to be easily moved. Another objective of the present invention is to teach the users how to stand straight, keep the body aligned, and maintain a proper weight distribution. Additional advantages of the invention can set forth in part in the description which follows, and in part can be obvious from the description, or may be learned by practice of the invention. Additional advantages of the invention may be realized and attained by means of the instrumentalities and combinations particularly pointed out in the detailed description of the invention section. Further benefits and advantages of the embodiments of the invention can become apparent from consideration of the following detailed description given with reference to the accompanying drawings, which specify and show preferred embodiments of the present invention.

SUMMARY OF THE INVENTION

The present invention is a posture correction and weight balance apparatus that teaches users how to have proper balance, coordination, and posture in order to fix or avoid back problems. The present invention provides a foam padding for the user to rest their body against, so the user can learn to stand correctly. The present invention further provides a reflective body that allows the user to visualize their body coordination. The present invention further provides a scale body for the user to stand on, so the user can learn to properly distribute their weight on both feet in order to prevent undue strain on the lower back. By teaching users how to stand correctly, users should avoid a hump back condition as they get older. The present invention takes into account all three key aspects of proper body posture and helps users avoid any posture related problems. A plurality of guidelines that can be positioned vertically and/or horizontally on the foam padding further allows the user to visualize proper body posture and alignment. A personalized treatment program can be further to instruct optimal treatment after utilizing the present invention.

DETAIL DESCRIPTIONS OF THE INVENTION

Figure 1:
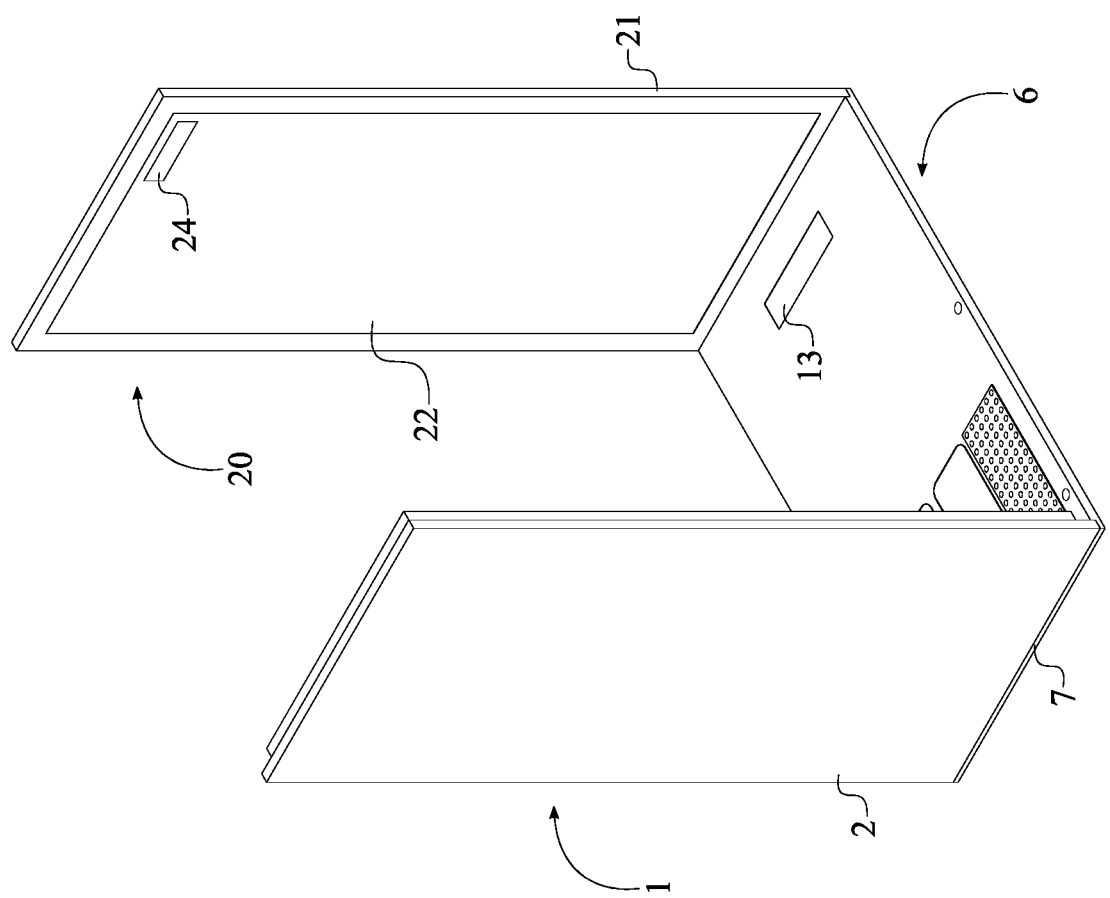
FIG. 1 is a perspective view of the present invention, showing the reflective body.
Figure 2:
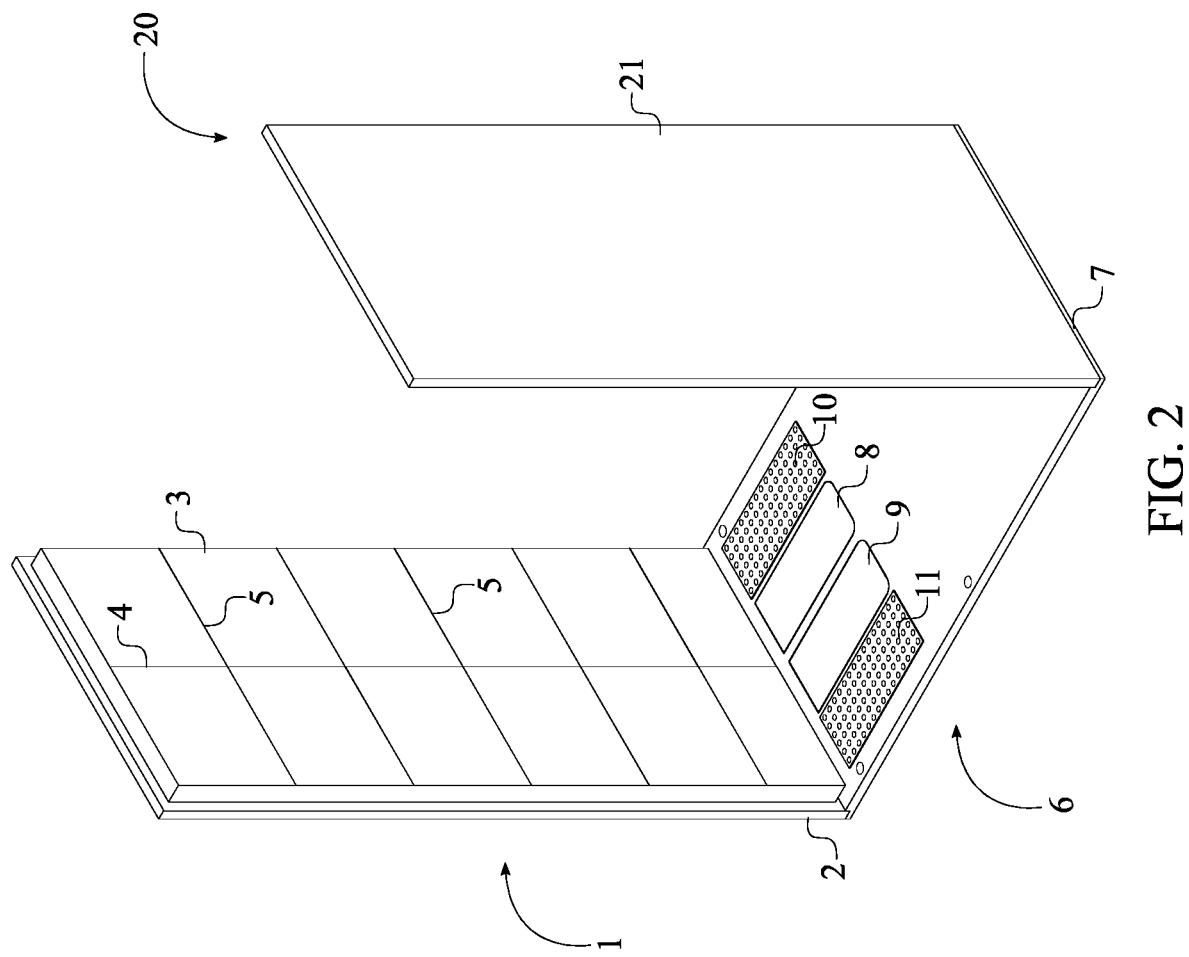
FIG. 2 is a perspective view of the present invention, showing the back support.
Figure 3:
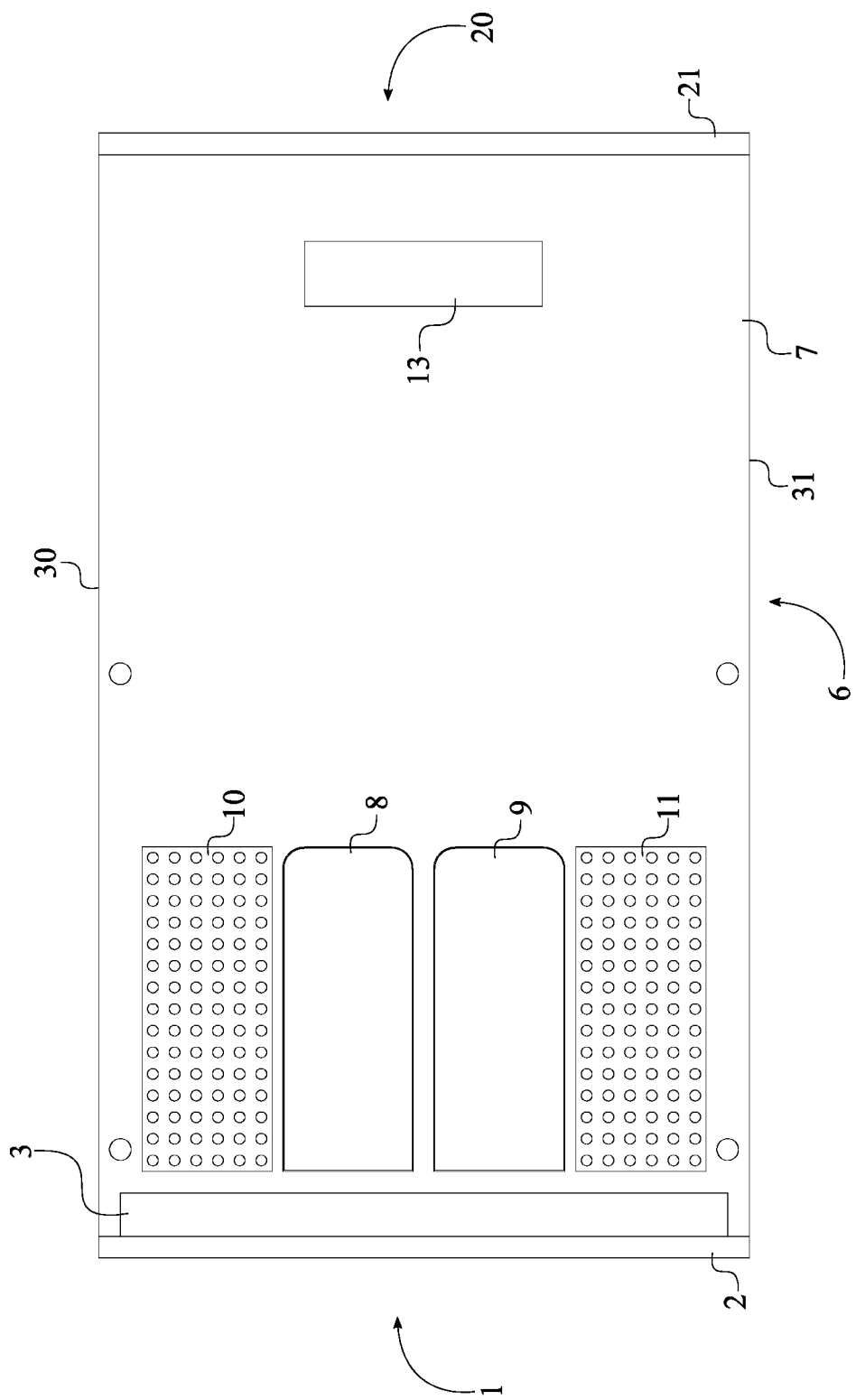
FIG. 3 is a top view of the present invention.

All illustrations of the drawings are for the purpose of describing selected versions of the present invention and are not intended to limit the scope of the present invention.

The present invention is a posture correction and weight balance apparatus, which is affiliated with the trademark name "Ultimate Posture Program". More specifically, the present invention teaches users how to have proper balance, body coordination, and body posture thus preventing or fixing many back problems that can occur due to improper standing. The present invention further provides a weight distribution of the user's body with respect to the left side and the right side thus enabling the users retrain their body according to even weight distribution.

In reference to FIG. 1-3 and FIG. 5, the present invention comprises a back support 1, a scale body 6, and a reflective body 20 as the main modular components. The scale body 6 comprises a base 7, a left platform 8, a right platform 9, a first power source 12, at least one first display 13, a left weight sensor 14, and a right weight sensor 15. More specifically, the back support 1 and the reflective body 20 are oppositely positioned of each other about the scale body 6 in such a way that the back support 1 and the reflective body 20 are positioned perpendicular to the base 7. A support panel 2 of the back support 1 is terminally attached to the base 7 so that the back support 1 and the base 7 can be easily disassembled from one end. A frame 21 of the reflective body 20 is terminally attached to the base 7 and positioned opposite of the back support 1 so that the reflective body 20 and the base 7 can be easily disassembled from the opposite end. The left platform 8 and the right platform 9 are adjacently aligned across the back support 1 and mounted onto the base 7. The left platform 8 and the right platform 9 function as a weight measuring scale so that the measured weight can be displayed on the at least one first display 13 that is positioned adjacent to the reflective body 20 and mounted onto the base 7. The left platform 8 is electronically connected to the at least one first display 13 through the left weight sensor 14. The right platform 9 is electronically connected to the at least one first display 13 through the right weight sensor 15. Resultantly, the left platform 8 and the right platform 9 can individually measure the body weight with respect to the left side and the right side of the user's body. Furthermore, the left platform 8 and the right platform 9 also measure the total body weight of the user's body.

Figure 8:
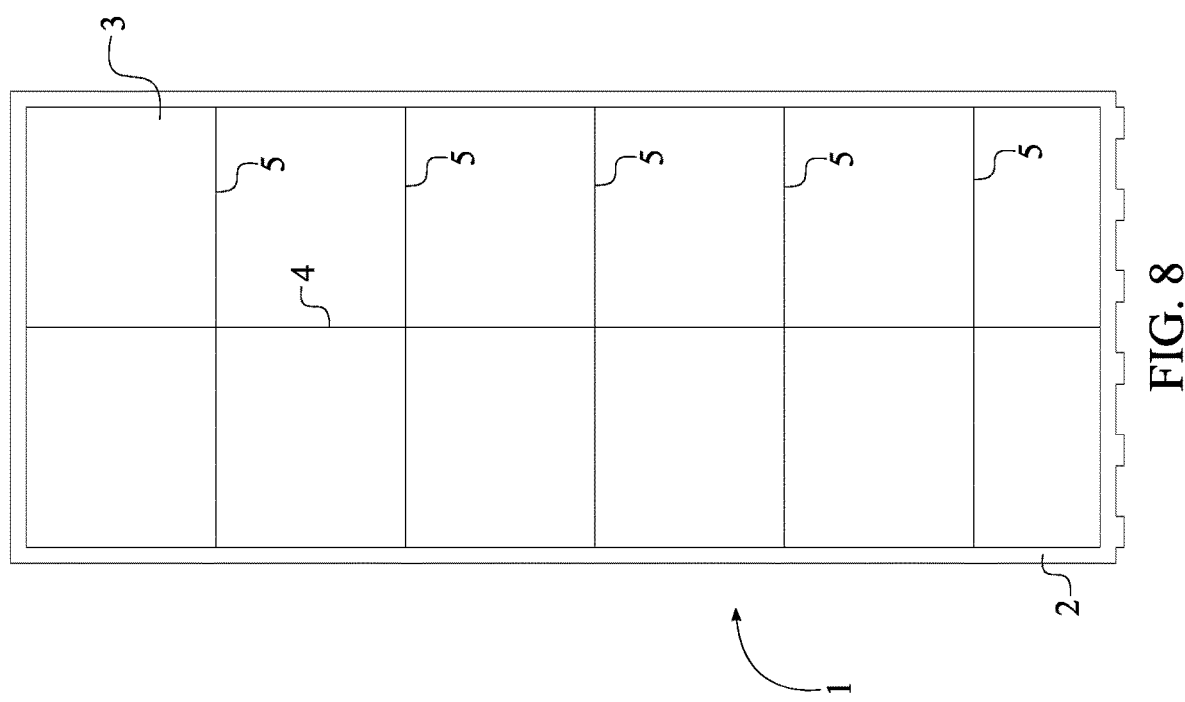
FIG. 8 is a front view of the back support of the present invention, showing the mid-sagittal guideline and the plurality of horizontal guidelines.

The back support 1 receives the body of the user so that the user's body posture can be straighten and conditioned to maintain a correct posture. In reference to FIG. 8, the back support 1 is an upright vertical and elongated body that further comprises at least one foam padding 3, a mid-sagittal guideline 4, and a plurality of horizontal guidelines 5. More specifically, the support panel 2 is a rigid body and is perpendicularly attached to the base 7 so that the support panel 2 can withstand the weight of the user's body when the user stands up against the back support 1. The preferred embodiment of the present invention utilizes a plurality of mortise and tenon attachments to perpendicularly attach the back support 1 to the scale body 6. However, the present invention is not limited to the aforementioned attachments and can utilize any other type of easily detachable fastening mechanism to secure the back support 1 to the scale body 6. The at least one foam padding 3 is perimetrically attached onto the support panel 2 is oriented toward the reflective body 20. The at least one foam padding 3 provides a comfortable and orthopedic surface area to rest the user's body in the upright position. In the preferred embodiment of the present invention, the at least one foam padding 3 is a lightweight and viscoelastic polyurethane foam to optimize the comfort level. The mid-sagittal guideline 4 is centrally positioned along the at least one foam padding 3. The plurality of horizontal guidelines 5 is positioned across the at least one foam padding 3, wherein the plurality of horizontal guidelines 5 is perpendicularly positioned to the mid-sagittal guideline 4. The mid-sagittal guideline 4 and the plurality of horizontal guidelines 5 allow the user to determine if their posture is properly and symmetrically aligned. For example, the mid-sagittal guideline 4 and the plurality of horizontal guidelines 5 allow the user to see if the hips and shoulders are properly and lineally aligned with each other.

The scale body 6 is an elongated body and provides a platform for the user to stand upon. The scale body 6 also provides a way and method for the user to track the weight distribution on their feet and helps the user to correct any misdistribution. In reference to FIG. 7, FIG. 10, and FIG. 11, the left platform 8 is positioned adjacent to a left side of the base 7 so that the user can place their left foot to measure the body weight. Similarly, the right platform 9 is positioned adjacent to a right side of the base 7 so that the user can place their right foot to measure the body weight. In other words, the left platform 8 and the right platform 9 provide two separate designated areas with the scale body 6. The left platform 8 is electronically connected to the left weight sensor 14. The right platform 9 is electronically connected to the right weight sensor 15. As a result, the left weight sensor 14 and the right weight sensor 15 are able to measure the body weight of the user. A chipset 19 of the present invention is able to process the readings from the left weight sensor 14 and the right weight sensor 15 and displays in the at least one first display 13. More specifically, the chipset 19 is enabled to execute the aforementioned process as the left weight sensor 14 and the right weight sensor 15 are electronically connected to the chipset 19, and the chipset 19 is electronically connected to the at least one first display 13. In order to the measure the user's body through the left platform 8, the left weight sensor 14 is mounted within the base 7 in such a way that the left weight sensor 14 is positioned adjacent and below the left platform 8. In order to measure the user's body through the right platform 9, the right weight sensor 15 is mounted within the base 7 in such a way that the right weight sensor 15 is positioned adjacent and below the right platform 9. The chipset 19 and the first power source 12 are mounted within the base 7 to protect from outside elements. Furthermore, the chipset 19, the left weight sensor 14, and the right weight sensor 15 are electrically connected to the first power source 12 so that the first power source 12 can electrically power these components. Optionally, the scale body 6 can comprise an alarm unit. The alarm unit is electronically connected to the chipset 19 and electrically powered with the first power source 12 so that the alarm unit can release an audio file to warn about the uneven weight distribution or other problems that may detect.

Figure 7:
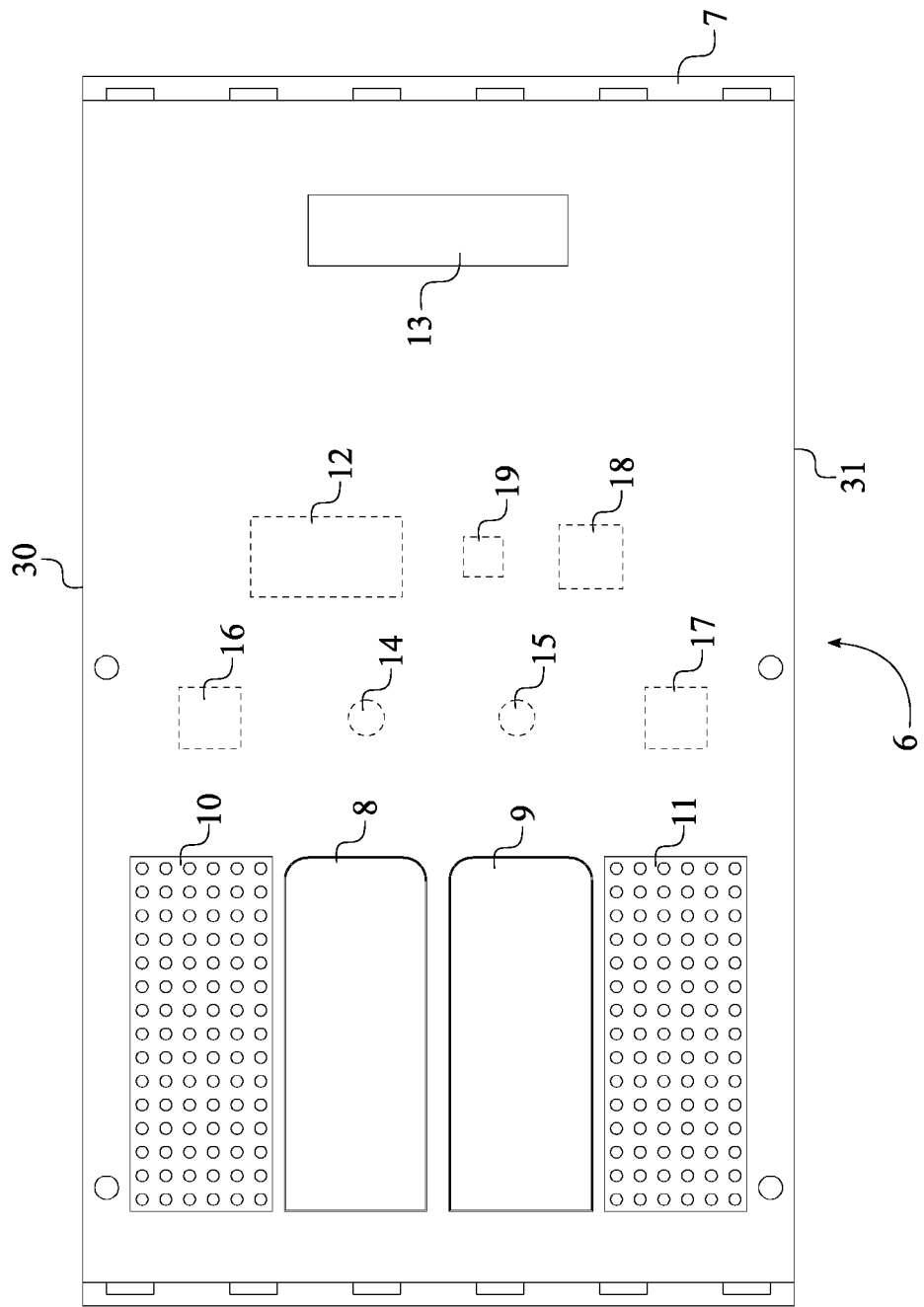
FIG. 7 is a top view of the scale body of the present invention, wherein the dash lines illustrate the internal components of the scale body.
Figure 11:
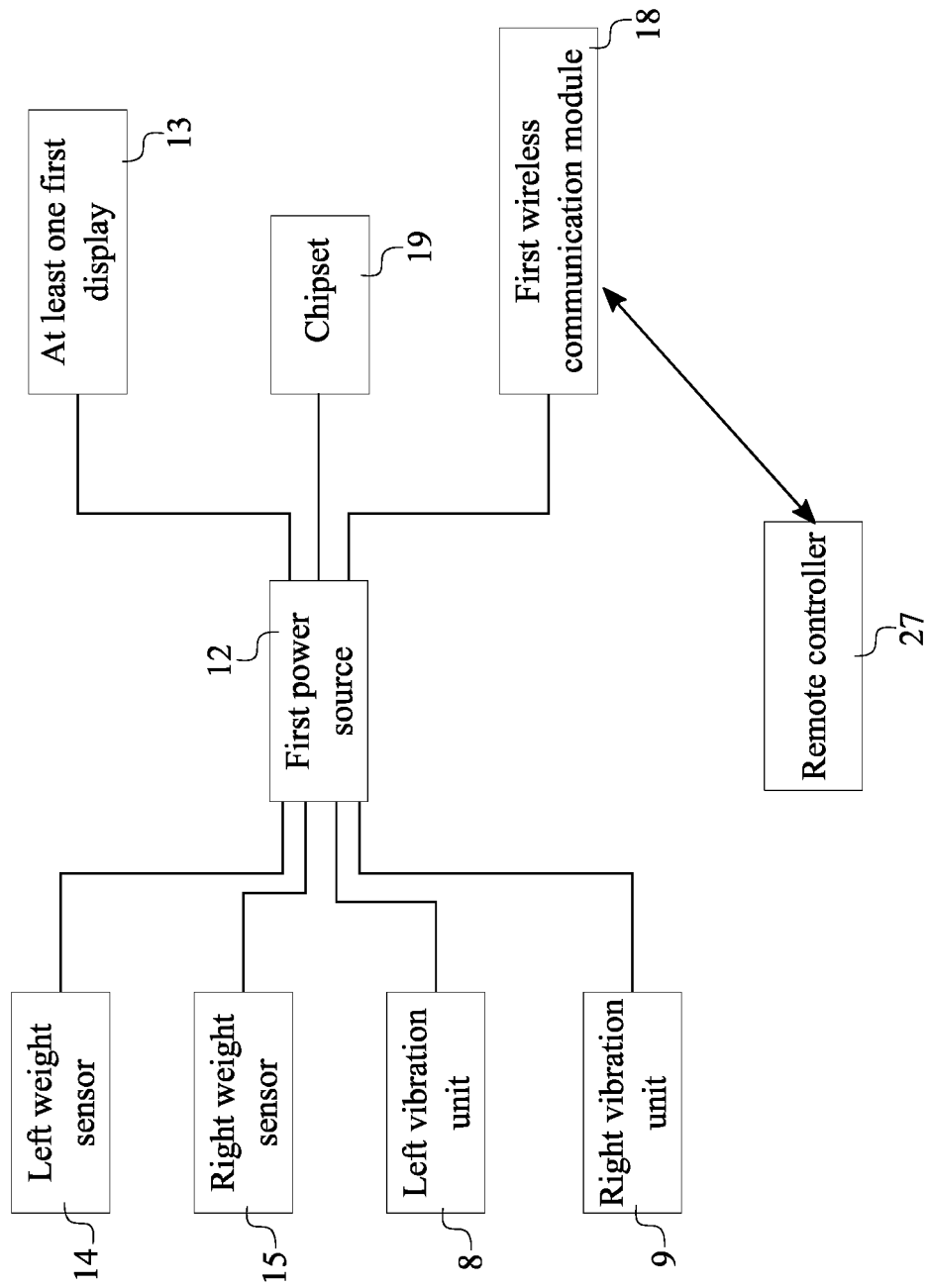
FIG. 11 is a basic schematic view of the present invention showing the electrical connections to the first power source.

In reference to FIG. 7 and FIG. 11, the present invention further comprises a first wireless communication module 18. More specifically, the first wireless communication module 18 is mounted within the base 7 to protect from outside elements. The first wireless communication module 18 electronically connected to the chipset 19 so that the readings from the left weight sensor 14 and the right weight sensor 15 can be wirelessly transmitted into at least one second display 24 of the reflective body 20. In order to execute the wireless transmission of the readings, the first wireless communication module 18 is communicably coupled with the second wireless communication. Furthermore, the first wireless communication module 18 is electrically connected to the first power source 12 so that the first wireless communication module 18 can be electrically powered. Furthermore, the at least one display 13 is electrically connected to the first power source 12 so that the at least one display 13 can be electrically powered.

Figure 10:
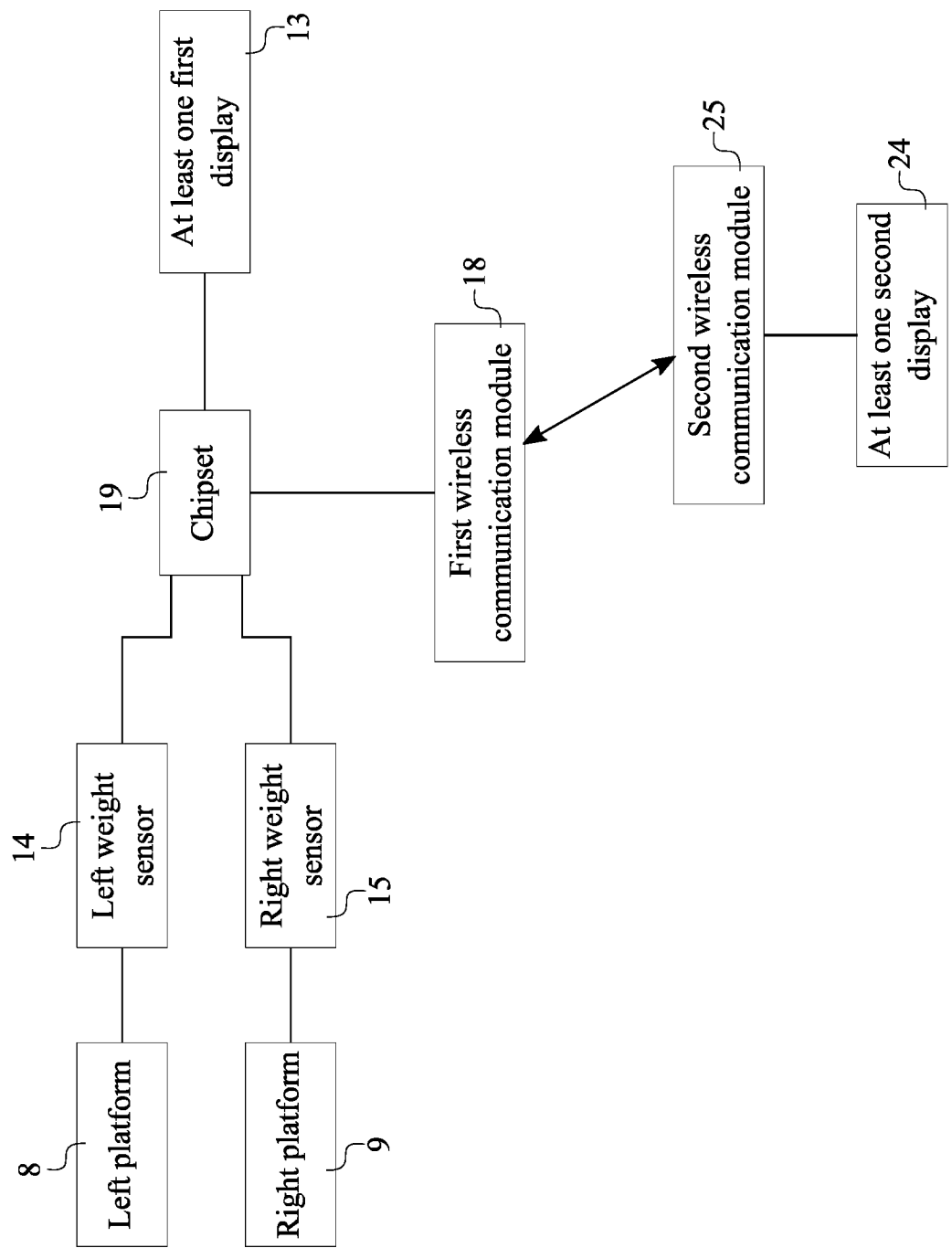
FIG. 10 is a basic schematic view of the present invention showing the electronical connections.

In reference to FIG. 7, FIG. 10, and FIG. 11, the present invention further comprises a left vibrating board 10, a right vibrating board 11, a left vibration unit 16, and a right vibration unit 17. The left vibration board and the right vibration board function as strength and coordination teaching mechanism within the present invention. The left vibration board and the right vibration board also allow patients to improve their proprioception, which is their ability to know where they are in time and in space. The left vibration board and the right vibration board also beneficial for patients who have had strokes or have lost the ability to feel anything in their legs due to disc degeneration, spinal stenosis, or other low back injuries. More specifically, the left vibrating board 10 is positioned adjacent to the left side of the base 7 so that the user can place their left or right foot on the left vibrating board 10. Similarly, the right vibrating board 11 is positioned adjacent to the right side of the base 7 so that the user can place their left or right foot on the right vibrating board 11. In other words, the left vibrating board 10 and the right vibrating board 11 provide two separate designated areas with the scale body 6. In order to attain proper balance and correct shoulder length during usage, the left vibrating board 10 and the right vibrating board 11 are positioned outside of the left platform 8 and right platform 9. Due to the adjacent positioning of the left vibration board and the right vibration board, the user can simply move their legs and feet slightly lateral from the left platform 8 and the right platform 9 thus providing a better formation to perform the vibrating functionality. The left vibrating board 10 is operatively coupled to the left vibration unit 16, wherein the left vibration unit 16 rhythmically moves back and forth the left vibrating board 10. The left vibration unit 16 is mounted within the base 7 and positioned adjacent to the left vibrating board 10. Furthermore, the left vibration unit 16 is electrically connected to the first power source 12 so that the electric energy can be converted into mechanical energy. The right vibrating board 11 is operatively coupled to the right vibration unit 17, wherein the right vibration unit 17 rhythmically moves back and forth the right vibrating board 11. The right vibration unit 17 is mounted within the base 7 and positioned adjacent to the right vibrating board 11. Furthermore, the right vibration unit 17 is electrically connected to the first power source 12 so that the electric energy can be converted into mechanical energy.

In reference to FIG. 11, the present invention further comprises a remote controller 27 that is communicably coupled with the first wireless communication module 18 so that the remote controller 27 can wirelessly operate the left vibration unit 16 and the right vibration unit 17. In the preferred embodiment of the present invention, the remote controller 27 comprises a first button, a second button, and a plurality of control buttons. The first button, preferably colored as a green button, is positioned at the top of the remote controller 27. By pressing the first button, the user can turn on the left vibrating unit and the right vibrating unit which simultaneously activate the left vibration board and the right vibration board. The second button, preferably colored as a red button and larger than other two buttons, is positioned at the middle of the remote controller 27. By pressing the second button, the user can turn off the left vibrating unit and the right vibrating unit which gradually deactivate the left vibration board and the right vibration board. The plurality of control buttons allows the user to control the rate of vibration within the present invention. More specifically, the user can increase the rate of the vibration by moving along the plurality of control buttons to the right and decrease the rate of vibration by moving along the plurality of control buttons to the left. The remote controller 27 is a small device and can be held in the user's hand; however, the remote controller 27 can also have a strap so that the strap can be wrapped around the user's wrist. If the user lose their balance while using the left vibrating board 10 and the right vibrating board 11, the user can easily access the remote controller 27 for stoppage of the left vibrating board 10 and the right vibrating board 11.

The reflective body 20 enables the user to see their body and see any misalignments from the mid-sagittal guideline 4 and the plurality of horizontal guidelines 5. In reference to FIG. 9, the reflective body 20 further comprises a reflective surface 22, a second power source 23, and a second wireless communication module 25 in addition to the frame 21 and the at least one second display 24. The reflective surface 22 is perimetrically connected onto the frame 21 as the reflective surface 22 is oriented toward the back support 1. More specifically, the reflective surface 22 is a thin body with reflective properties on the front surface as the frame 21 perimetrically holds and protects the reflective surface 22. The reflective surface 22 can include, but is not limited to, glass, reflective film, or any similar reflective material.

Figure 9:
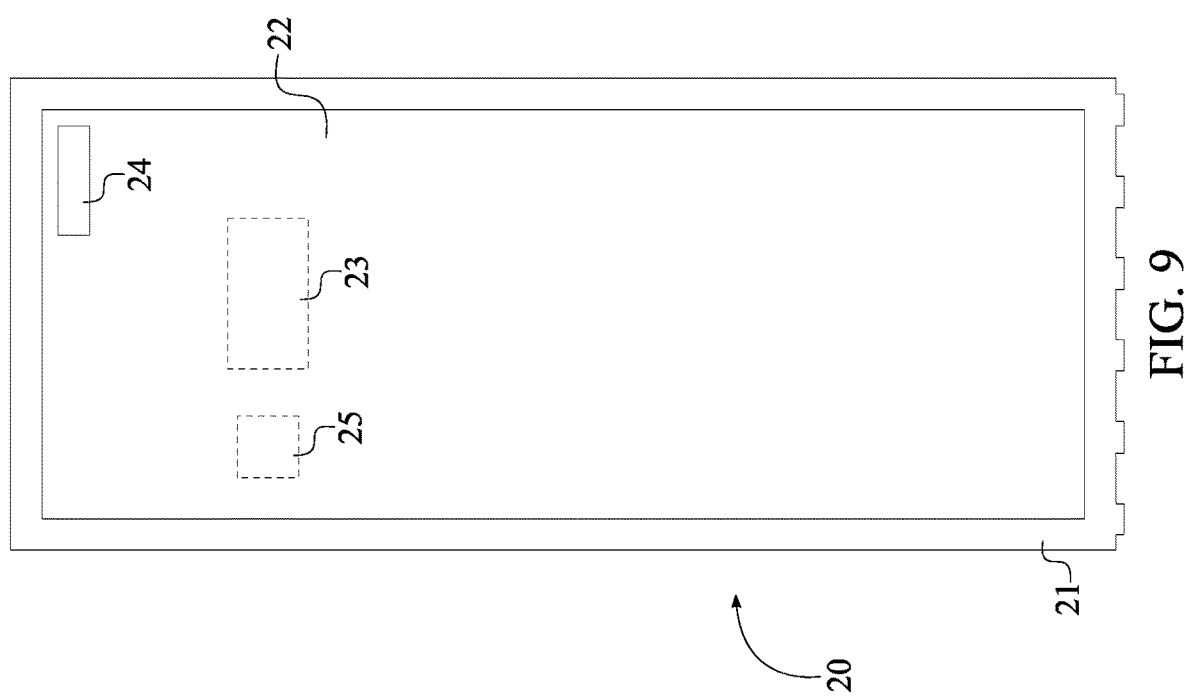
FIG. 9 is a front view of the reflective body of present invention, wherein the dash lines illustrate the internal components of the reflective body.
Figure 12:
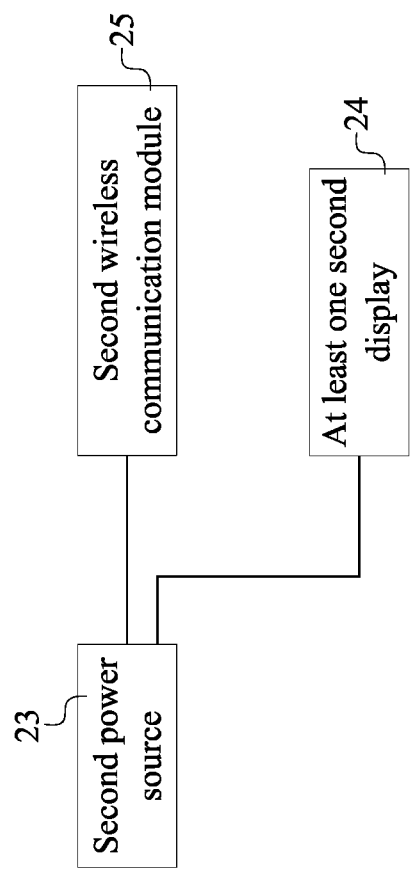
FIG. 12 is a basic schematic view of the present invention showing the electrical connections to the second power source.

In reference to FIG. 9, FIG. 10, and FIG. 12, the at least one second display 24 is integrated onto the reflective surface 22 so that readings from the at least one first display 13 can be wirelessly transmitted onto the reflective surface 22. The second wireless communication module 25 is mounted within the frame 21 so that the at least one second display 24 can be electronically connected to the second wireless communication module 25 within the frame 21. More specifically, the readings that are displayed within the at least one first display 13 is first received by the second wireless communication module 25. The readings are then transmitted into the at least one second display 24 from the second wireless communication module 25 to be displayed. The second power source 23, preferably a disposable or rechargeable battery, is mounted within the frame 21. As a result, the at least one second display 24 and the second wireless communication module 25 are electrically connected to the second power source 23 thus providing electrical power to the components.

Figure 6:
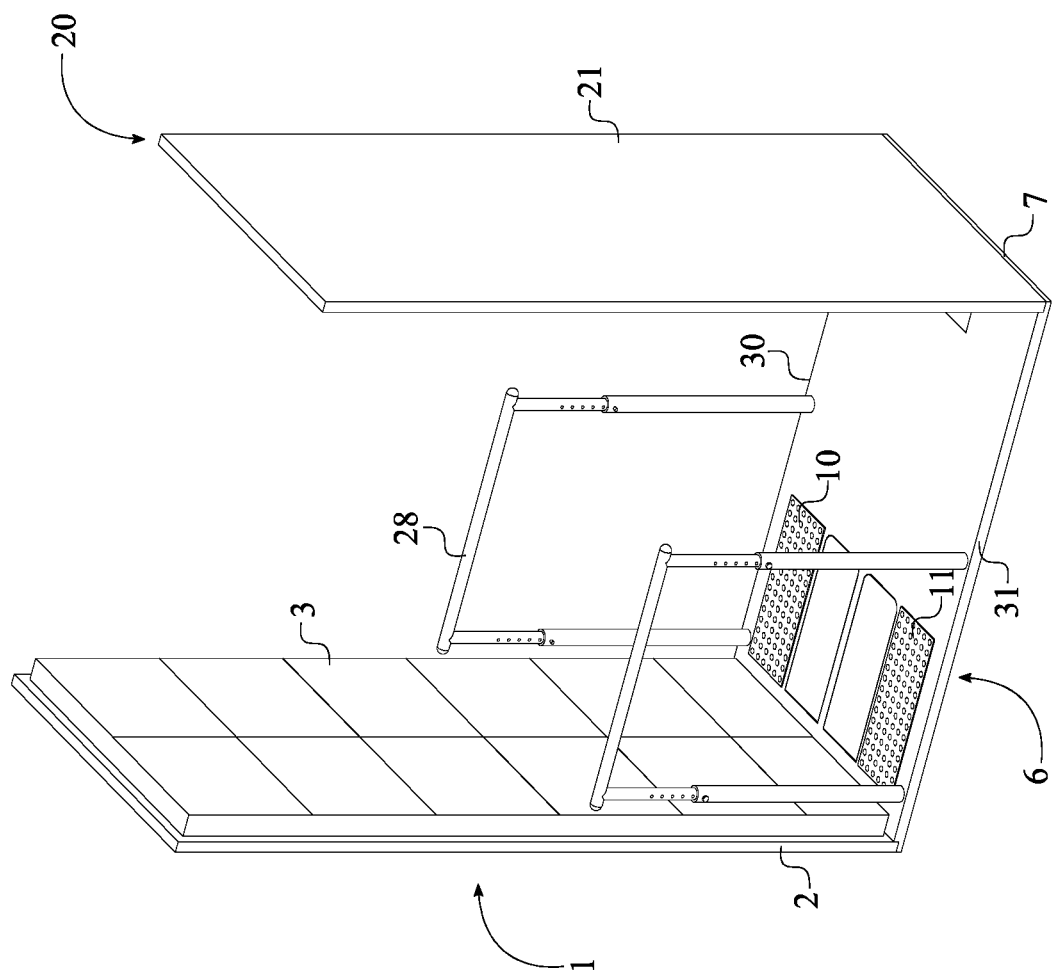
FIG. 6 is a perspective view of the present invention, wherein the left railing and the right railing is mounted to the base.

In reference to FIG. 6, the present invention further comprises a left railing 28 and a right railing 29. The left railing 28 is removably mounted to the left side of the base 7, and the right railing 29 is removably mounted to the right side of the base 7. The left railing 28 and the right railing 29 functions as safety measures if the user feels insecure or lose their balance. For example, the user grip on the left railing 28 and the right railing 29 when the user begins to lose their balance or coordination. The left railing 28 and the right railing 29 also have the ability to adapt any height from the scale body 6 to accommodate different user heights as each railing functions as a telescopic body that can be locked at different heights.

Figure 4:
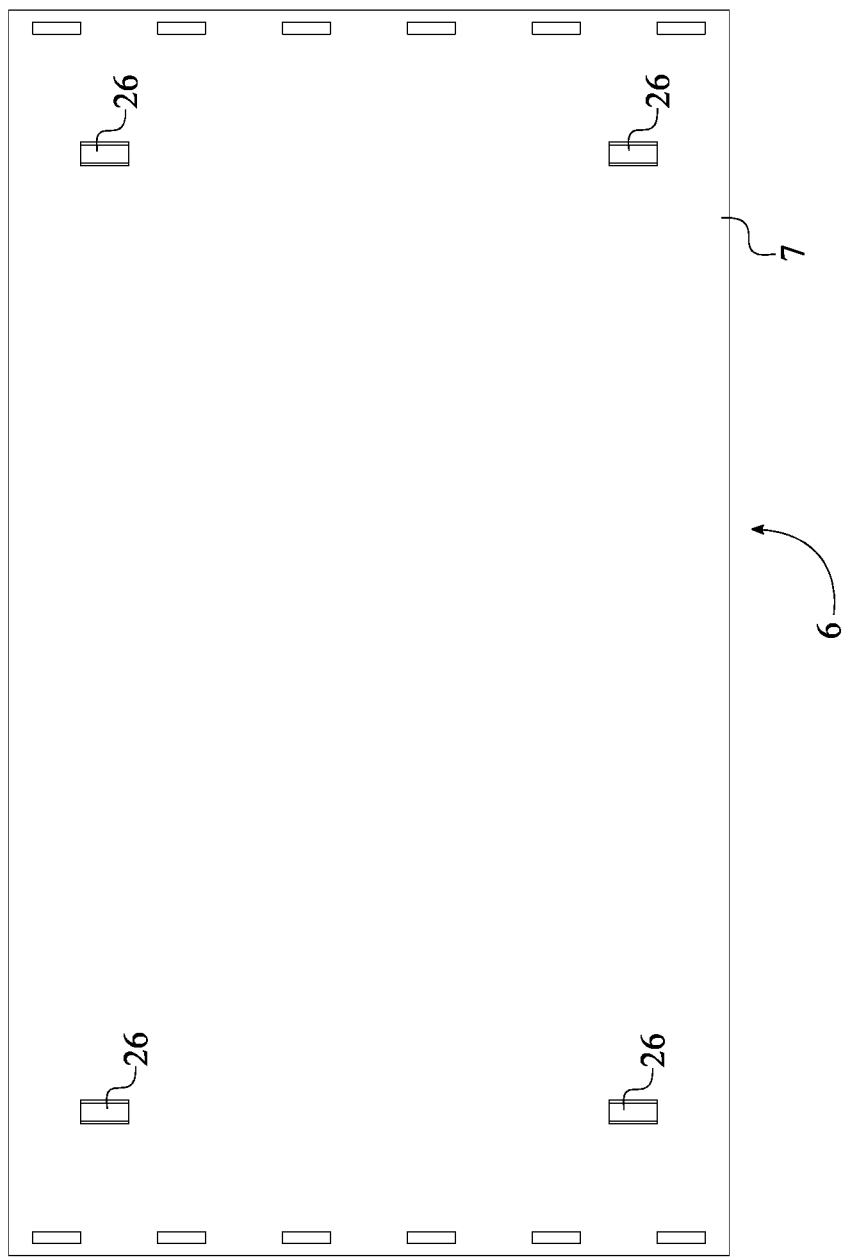
FIG. 4 is a bottom view of the present invention.
Figure 5:
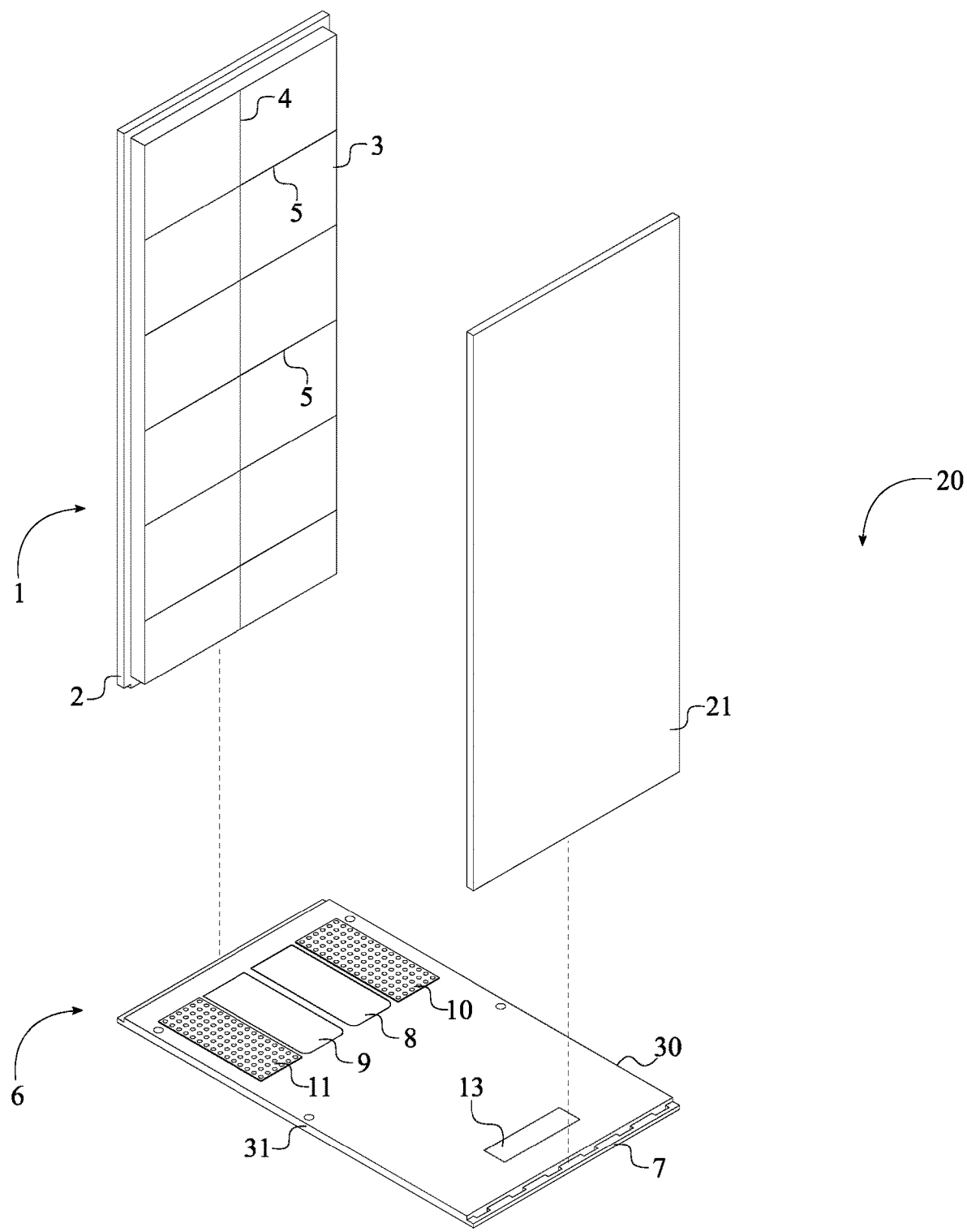
FIG. 5 is an exploded view of the present invention.

In reference to FIG. 4, the present invention further comprises a plurality of wheels 26 that is rotatably connected to the base 7, opposite of the at least one first display 13. In other words, the plurality of wheels 26 is positioned on a bottom surface of the base 7 so that the present invention can be easily moved to different places.

Furthermore, the first wireless communication module 18 is able to communicably couple with a remote database or a computing device to wirelessly transmit the readings from the chipset 19. As a result, the readings can be chronologically transmitted to the remote database 7 or the computing device with a timestamp to track and monitor the progress of the ongoing therapy sections or to correct and train body posture. Once the readings of a patient are attained through the present invention, a medical professional can generate a customized medical treatment program for the attained readings. The patient is then put thought the customized medical treatment program in order to overcome their existing health problems or potential health problems that are concluded by the medical professional.

Although the invention has been explained in relation to its preferred embodiment, it is to be understood that many other possible modifications and variations can be made without departing from the spirit and scope of the invention as hereinafter claimed.

What is claimed is:

1. A posture correction and weight balance apparatus comprises:
    a back support;
    a scale body;
    a reflective body;
    the scale body comprises a base, a left platform, a right platform, a first power source, at least one first display, a left weight sensor, and a right weight sensor;
    the back support and the reflective body being oppositely positioned of each other about the scale body;
    the back support and the reflective body being positioned perpendicular to the base;
    a support panel of the back support being terminally attached to the base;
    a frame of the reflective body being terminally attached to the base, opposite of the back support;
    the left platform and the right platform being adjacently aligned across the back support;
    the left platform and the right platform being mounted onto the base;
    the at least one first display being positioned adjacent to the reflective body;
    the at least one first display being mounted onto the base;
    the left platform being electronically connected to the at least one first display through the left weight sensor;
    the right platform being electronically connected to the at least one first display through the right weight sensor;
    the back support further comprises at least one foam padding, a mid-sagittal guideline, and a plurality of horizontal guidelines;
    the support panel being perpendicularly attached to the base;
    the at least one foam padding being perimetrically attached onto the support panel;
    the at least one foam padding being oriented toward the reflective body;
    the mid-sagittal guideline being centrally positioned along the at least one foam padding;
    the plurality of horizontal guidelines being positioned across the at least one foam padding; and
    the plurality of horizontal guidelines being perpendicularly positioned to the mid-sagittal guideline.

2. The posture correction and weight balance apparatus as claimed in claim 1 comprises:
    the reflective body further comprises a reflective surface;
    the reflective surface being perimetrically connected onto the frame; and
    the reflective surface being oriented toward the back support.

3. The posture correction and weight balance apparatus as claimed in claim 1 comprises:
    the reflective body further comprises a reflective surface, a second power source, at least one second display, and a wireless communication module;
    the at least one second display being integrated onto the reflective surface;
    the wireless communication module being mounted within the frame;
    the second power source being mounted within the frame;
    the at least one second display and the wireless communication module being electrically connected to the second power source; and
    the at least one second display being electronically connected with the wireless communication module.

4. The posture correction and weight balance apparatus as claimed in claim 1, wherein the first power source being mounted within the base.

5. The posture correction and weight balance apparatus as claimed in claim 1 comprises:
    a chipset;
    the left platform being positioned adjacent to a left side of the base;
    the right platform being positioned adjacent to a right side of the base;
    the left platform being electronically connected to the left weight sensor;
    the right platform being electronically connected to the right weight sensor;
    the left weight sensor and the right weight sensor being electronically connected to the chipset; and
    the chipset being electronically connected to the at least one first display.

6. The posture correction and weight balance apparatus as claimed in claim 5 comprises:
    the left weight sensor being mounted within the base;
    the left weight sensor being positioned adjacent to the left platform; and
    the left weight sensor being electrically connected to the first power source.

7. The posture correction and weight balance apparatus as claimed in claim 5 comprises:
    the right weight sensor being mounted within the base;
    the right weight sensor being positioned adjacent to the right platform; and
    the right weight sensor being electrically connected to the first power source.

8. The posture correction and weight balance apparatus as claimed in claim 5 comprises:
    the chipset being mounted within the base; and
    the chipset being electrically connected to the first power source.

9. The posture correction and weight balance apparatus as claimed in claim 5 comprises:
    a first wireless communication module;
    the first wireless communication module being mounted within the base;
    the first wireless communication module being electronically connected to the chipset;
    the first wireless communication module being communicably coupled with a second wireless communication module of the reflective body;
    the first wireless communication module being electrically connected to the first power source; and
    the at least one display being electrically connected to the first power source.

10. The posture correction and weight balance apparatus as claimed in claim 1 comprises:
    a left vibrating board;
    a right vibrating board;
    a left vibration unit;
    a right vibration unit;
    a chipset;
    the left vibrating board being positioned adjacent to a left side of the base;

the left vibrating board being operatively coupled to the left vibration unit, wherein the left vibration unit rhythmically moves back and forth the left vibrating board;

the right vibrating board being positioned adjacent to a right side of the base; and the right vibrating board being operatively coupled to the right vibration unit, wherein the right vibration unit rhythmically moves back and forth the right vibrating board.

11. The posture correction and weight balance apparatus as claimed in claim 10 comprises:

the left vibration unit being mounted within the base;

the left vibration unit being positioned adjacent to the left vibrating board; and the left vibration unit being electrically connected to the first power source.

12. The posture correction and weight balance apparatus as claimed in claim 10 comprises:

the right vibration unit being mounted within the base;

the right vibration unit being positioned adjacent to the right vibrating board; and the right vibration unit being electrically connected to the first power source.

13. The posture correction and weight balance apparatus as claimed in claim 1 comprises:

a remote controller;

a first wireless communication module; and the remote control being communicably coupled with the first wireless communication module, wherein the remote control wirelessly operates a left vibration unit and a right vibration unit.

14. The posture correction and weight balance apparatus as claimed in claim 1 comprises:

a left railing;

a right railing;

the left railing being removably mounted to a left side of the base; and the right railing being removably mounted to a right side of the base.

15. The posture correction and weight balance apparatus as claimed in claim 1 comprises:

a plurality of wheels; and the plurality of wheels being rotatably connected to the base, opposite of the at least one first display.

* * * * *